United States Patent [19]

Quincy, III et al.

[11] Patent Number: 5,500,254

[45] Date of Patent: Mar. 19, 1996

[54] COATED POLYMERIC FABRIC HAVING DURABLE WETTABILITY AND REDUCED ADSORPTION OF PROTEIN

[75] Inventors: Roger B. Quincy, III, Alpharetta; Ronald S. Nohr, Roswell; John G. MacDonald, Decatur; Elizaeth D. Gadsby, Marietta; Dennis S. Everhart, Alpharetta, all of Ga.

[73] Assignee: Kimberly-Clark Corporation, Neenah, Wis.

[21] Appl. No.: 170,598

[22] Filed: Dec. 21, 1993

[51] Int. Cl.$^6$ ............................... B32B 27/00; B32B 9/00
[52] U.S. Cl. ................... 427/387; 427/388.4; 427/389.9; 427/397.7; 428/266; 428/290; 428/903; 428/289
[58] Field of Search ..................................... 428/266, 290, 428/913, 903; 427/387, 388.4, 389.9, 397.7

[56] References Cited

U.S. PATENT DOCUMENTS

| | | | |
|---|---|---|---|
| 3,341,394 | 9/1967 | Kinney | 161/72 |
| 3,802,817 | 4/1974 | Matsuki et al. | 425/66 |
| 4,152,273 | 5/1979 | Weiland | 252/8.8 |
| 4,293,611 | 10/1981 | Martin | 428/266 |
| 4,857,251 | 8/1989 | Nohr et al. | 264/103 |
| 4,859,529 | 8/1989 | Raleigh et al. | 428/290 |
| 4,920,168 | 4/1990 | Nohr et al. | 524/188 |
| 4,923,914 | 5/1990 | Nohr et al. | 524/99 |
| 5,039,420 | 8/1991 | Klein et al. | 210/645 |
| 5,057,361 | 10/1991 | Sayovitz et al. | 428/290 |
| 5,102,738 | 4/1992 | Bell et al. | 428/411.1 |
| 5,112,690 | 5/1992 | Cohen et al. | 428/411.1 |
| 5,139,877 | 8/1992 | Self et al. | 428/421 |
| 5,258,129 | 11/1993 | Kato et al. | 252/8.9 |
| 5,258,451 | 11/1993 | Ohsawa et al. | 524/755 |
| 5,283,023 | 2/1994 | Nohr et al. | 264/103 |

FOREIGN PATENT DOCUMENTS

| | | |
|---|---|---|
| 0372890 | 6/1990 | European Pat. Off. . |
| 0562620 | 9/1993 | European Pat. Off. . |
| 0598204 | 5/1994 | European Pat. Off. . |
| 2110114 | 6/1983 | United Kingdom . |
| 89/03851 | 5/1989 | WIPO . |
| 91/15952 | 10/1991 | WIPO . |

OTHER PUBLICATIONS

Abstract of JP 4902769A (Shin–Etsu Chem. Ind. Co.) Textile treatment using an aqueous solution of polysiloxane-p-olyether.

"TEGOPREN® Silicone Surfactants—Products, Data, Information", Th. Goldschmidt AG, Essen, Germany.

T. Pohl, "Concentration of Proteins and Removal of Solutes", Methods In Enzymology, vol. 182, 1990, pp. 68–83.

K. Bergstrom, et al., "Reduction of Fibrinogen Adsorption on PEG–Coated Polystyrene Surfaces." *Journal of Biomedical Materials Research*, vol. 26, 1992, pp. 779–790.

T. A. Horbett, et al., "The Kinetics of Baboon Fibrinogen Adsorption to Polymers: In Vitro and In Vivo Studies." *Journal of Biomedical Materials Research*, vol. 20, 1986, pp. 739–772.

E. Mihalyi, "Physicochemical Studies of Bovine Fibrinogen, IV. Ultra Violet Absorption & Its Relation to the Structure of the Molecule." Biochemistry, V. 7, No. 1, 1968, pp. 208–222.

M. S. Sheu, et al., "A Glow Discharge Treatment to Immobilize Poly(Ethylene Oxide)/Poly(Propylene Oxide) Surfactants for Wettable and Non–Fouling Biomaterial." *Journal Adhesion Sci. Technology*, vol. 6, No. 9, 1992, pp. 995–1009.

E. L. Chaikof, et al., "Platelet Interaction with Poly(Ethylene Oxide) Networks." AIChE Journal, Jul. 1990, V. 36, No. 7, pp. 994–1002.

M. S. Sheu, et al., "A New Gas Discharge Process for Preparation of Non–Fouling Surfaces On Biomat." Clinical Mat., pp. 41–45, 1993.

E. L. Chaikof, et al., "ESCA Studies of Cross–Linked Poly(Ethylene Oxide)/Polysiloxane Networks." *Journal of Colloid and Interface Science*, vol. 137, No. 2, Jul. 1990, pp. 340–349.

E. L. Chaikoff, et al., "Bulk Properties of Poly(Ethylene Oxide)/Polysiloxane Network." *Net Polymeric Material*, 1990 vol. 2, No. 2, pp. 125–147.

R. W. Pekala, et al., "Crosslinked Polyether/Polysiloxane Networks for Blook–Interfacing Applic." Biomat. Sep. 1986, V.7, pp. 372–378.

A. Z. Piao, et al., "Synthesis and characterization of Poly-(dimethylsiloxane)—Poly (Ethylene Oxide)—Heparin CBABC Type Block Copolymers." *Journal of Biomaterial Science Polymer Edn.*, 1990. vol. 1, No. 4, pp. 299–313.

C. Sung, et al., "Synthesis and Characterization of Polymer Net—Made from Poly (Ethylene Oxide) and Polysiloxane." *Biomedical Networks Macromolecular Chem.*, 1990, vol. 1, No. 4, pp. 266–268.

K. D. Park, et al. "PEO–Modified Surfaces—In Vitro, Ex Vivo, and In Vivo Blood Compatibility." *Poly(Ethylene Glycol) Chemistry: Biotechnical and Biomedical Applications*, 1992, pp. 283–301.

(List continued on next page.)

Primary Examiner—George F. Lesmes
Assistant Examiner—Helen F. Lee
Attorney, Agent, or Firm—William E. Maycock

[57] ABSTRACT

A method of durably rendering a polymeric fabric, e.g., a polyolefin fabric, wettable and resistant to protein adsorption. The method involves providing a polymeric fabric having a surface, applying to the surface of the polymeric fabric a composition which includes water and a surfactant adapted to durably render the polymeric fabric resistant to protein adsorption, and drying the polymeric fabric. The surfactant has a solubility in water at 20° C. no greater than about 5 percent by weight, based on the weight of the water, and is present on the polymeric fabric in an amount of the surfactant sufficient to reduce the adsorption of the protein by the fabric. The coated fabric not only exhibits durable reduced adsorption of protein but also has durable wettability by aqueous liquids. The coated fabric is especially suited for incorporation in such disposable absorbent articles as diapers, feminine care products, such as sanitary napkins and tampons, incontinent care products, training pants, wipes, and the like.

2 Claims, 6 Drawing Sheets

OTHER PUBLICATIONS

T. A. Horbett, "Adsorption of Proteins from plasma to a series of hydrophilic–hydrophobic copolymers. II. Compositional analysis with the prelabeled protein technique." *Journal of Biomedical Materials Research*, vol. 15, 1981, pp. 673–695.

P. K. Weathersby, "Solution Stability of Bovine Fibrinogen." Thrombosis Research, vol. 10, No. 2, 1977, pp. 245–252.

J. L. Bohnert, et al. "Plasma Gas Dishcarge Deposited Fluorocarbon Polymers Exhibit Reduced Elutability of Adsorbed Albumin and Fibrinogen." *Journal of Biomaterial Science Polymer Edn.*, vol. 1, No. 4, 1990. pp. 279–297.

E. L. Chaikof, "Polyethylene Oxide/Polysiloxane Interpenetrating Polymer Networks For Blood Contact." *Massachusetts Institute of Tehnology*, (Submitted in partial fulfillment of the requirements for the Degree of Doctor of Philosophy), pp. 1–2 [Abstract].

C. Sung, "A Study of Polyethylene Oxide–Polysiloxane Networks as Biomaterials for Drug Release." *Massachusetts Institute of Tech.*, (Submitted in partial fulfillment of the requirements for the Degree of Doctor of Philosophy), 1988, pp. 1–2. [Abstract].

Technical Data Sheet—ABIL® B 88184.
Technical Data Sheet—ABIL® B 8842 & 88183.
Technical Data Sheet—ABIL® B 8857.
Technical Bulletin—SILWET® Surfactants For Use In Textiles.
Technical Bulletin—SILWET™ Surfactants—Physical Properties.
Technical Bulletin—SILWET® Surfactants —Structural Information Typical Performance Data.
Technical Bulletin—SILWET® Surfactants Uses.
Technical Data Sheet—SILWET® Surfactants For Use In Coatings.
Technical Data Sheet—SILWET® Surfactants For Use In Personal Care.
Technical Data Sheet—SILWET® Surfactants For Use In Printing Inks.
Technical Data Sheet—SILWET® Surfactants For Use In Diverse Markets.
"SILWET® Surfactants." Union Carbide Corp, Danbury, CT., pp. 1–15.

COATED POLYMERIC FABRIC HAVING DURABLE WETTABILITY AND REDUCED ADSORPTION OF PROTEIN

BACKGROUND OF THE INVENTION

The present invention relates to a coated polymeric fabric.

Polymers are used extensively to make a variety of products which include blown and cast films, extruded sheets, injection molded articles, foams, blow molded articles, extruded pipe, monofilaments, and nonwoven webs. Some of such polymers, such as polyolefins, are naturally hydrophobic, and for many uses this property is either a positive attribute or at least not a disadvantage.

There are a number of uses for polymers, however, where their hydrophobic nature either limits their usefulness or requires some effort to modify the surface characteristics of the shaped articles made therefrom. By way of example, polyolefins, such as polyethylene and polypropylene, are used to manufacture polymeric fabrics which are employed in the construction of such disposable absorbent articles as diapers, feminine care products, incontinence products, training pants, wipes, and the like. Such polymeric fabrics often are nonwoven webs prepared by, for example, such processes as meltblowing, coforming, and spunbonding. Frequently, such polymeric fabrics need to be wettable by water. Wettability can be obtained by spraying or otherwise coating (i.e., surface treating or topically treating) the fabric with a surfactant solution during or after its formation, and then drying the web.

Some of the more common topically applied surfactants are nonionic surfactants, such as polyethoxylated octylphenols and condensation products of propylene oxide with propylene glycol, by way of illustration only. These surfactants are effective in rendering normally hydrophobic polymeric fabrics wettable. However, the surfactant is readily removed from the fabric, often after only a single exposure to an aqueous liquid.

Substantial efforts have been directed to increasing the durability of surfactants which are topically applied to a polymeric fabric. Such efforts include the following, by way of illustration:

(1) use of a composition which includes water, a primary surfactant, and a cosurfactant which is functional to wet the fabric with the composition and which provides for substantially uniform distribution of the primary surfactant onto the polymeric fabric;

(2) use of a surfactant, with or without a nonionic cosurfactant, which is the reaction product of an acid anhydride derivative, such as a substituted succinic anhydride, with a polyhydroxy compound, such as sorbitol, a polyethylene glycol, triethanolamine, a polyhydroxyamine, certain primary and secondary amines, and certain unsaturated aliphatic sulfo compounds;

(3) use of a surfactant, with or without a nonionic cosurfactant, which is the reaction product of certain unsaturated aliphatic sulfo compounds with the reaction product of an acid anhydride derivative, such as a substituted succinic anhydride, with a polyamine having at least one NH group capable of addition to a double bond;

(4) use of a surfactant mixture which includes an ester-acid, ester salt, or a mixture thereof, and an amidic-acid, amidic salt, or mixture thereof, with or without a nonionic cosurfactant; and (5) use of a surfactant mixture which includes a sorbitol succinate surfactant, such as an ethoxylated amino sorbitol succinate salt or an alkenyl succinate anhydride ethoxylated fatty amine salt, and a cowetting aid which can be, for example, a silicone polyether or a primary or secondary alcohol having up to about 8 carbon atoms.

In addition to water wettability, another property of concern for many applications involving shaped articles made from polymers is the tendency of the shaped article to adsorb protein. For example, the adsorption of protein by polymeric fabrics which are employed in the construction of the disposable absorbent articles noted earlier can be a disadvantage. This is particularly true in the case of feminine care and other products which come in contact with blood and other protein-containing body fluids, some of which are colored. The adsorption of protein by a component of the product contributes to disapproval of the product for aesthetic reasons, even though the product may have superior performance in its intended function of fluid absorption and redistribution. More importantly, however, the adsorption of protein often reduces or prevents fluid absorption.

In the past, resistance to the adsorption of protein by a polymeric (or other) material has been accomplished by, for example, the radio frequency glow discharge plasma deposition of tetraethylene glycol dimethyl ether onto a polymeric material; coating of a polymeric material with polyethylene oxide-containing block copolymer surfactants or a polyethoxylated alkylphenol or longchain aliphatic alcohol, with or without a radio frequency argon glow discharge treatment after the polymeric material has been coated; immobilization of baboon albumin on radio frequency glow discharge-treated surfaces; radio frequency glow discharge polymerization of monomers on the surface of a material; a coating of a crosslinked polypropylene glycol/polyglycidoxy propyl methyl siloxane network which contains polyethylene glycol monomethyl ether chains; use of interpenetrating polymer networks of poly(ethylene oxide) and a polyether substituted polysiloxane; use of poly(dimethylsiloxane)-poly(ethylene oxide)-heparin CBABC type block copolymers; and use of immobilized poly(ethylene glycol) films.

Notwithstanding the advances which have been made in rendering a polymeric fabric wettable and in providing surfaces which are resistant to the adsorption of protein, there still is a need for further improvement in these areas. More particularly, a method is needed by which a polymeric fabric can be durably rendered wettable (or hydrophilic) and resistant to protein adsorption, by applying a surfactant to the fabric from an aqueous medium without the need for a subsequent radiation treatment.

SUMMARY OF THE INVENTION

It therefore is an object of the present invention to provide a method of durably rendering a polymeric fabric wettable and resistant to protein adsorption.

It is another object of the present invention to provide a coated polymeric fabric.

It is a further object of the present invention to provide a disposable absorbent article, at least one component of which is the coated polymeric fabric of the present invention.

These and other objects will be apparent to those having ordinary skill in the an from a consideration of the specification and claims which follow.

Accordingly, the present invention provides a method of durably rendering a polymeric fabric resistant to protein adsorption which includes:

providing a polymeric fabric having a surface;

applying to the surface of the polymeric fabric a composition which includes water and a surfactant adapted to durably render the polymeric fabric resistant to protein adsorption; and drying the polymeric fabric to which the composition has been applied; in which the surfactant has a solubility in water at 20° C. no greater than about 5 percent by weight, based on the weight of the water, and is present on the fabric in an amount sufficient to durably render the polymeric fabric resistant to protein adsorption.

The present invention also provides a method of durably rendering a polymeric fabric wettable and resistant to protein adsorption which includes:

providing a polymeric fabric having a surface;

applying to the surface of the polymeric fabric a composition which includes water and a surfactant; and drying the polymeric fabric to which the composition has been applied; in which the surfactant has a solubility in water at 20° C. no greater than about 5 percent by weight, based on the weight of the water, is present on the fabric in an amount sufficient to durably render the polymeric fabric wettable and resistant to protein adsorption, and has the general formula,

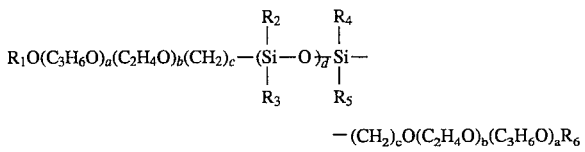

wherein:

each of $R_1$ and $R_6$ independently is selected from the group consisting of hydrogen and $C_1$–$C_8$ alkyl and aryl groups;

each of $R_2$–$R_5$ independently is selected from the group consisting of $C_1$–$C_8$ alkyl and aryl groups;

a represents an integer from about 8 to about 25;

b represents an integer from about 8 to about 25;

the ratio of b to a is in a range of from about 0.7 to about 1.5;

c represents an integer from 1 to about 10;

d represents an integer from about 40 to about 100;

the ratio of d to two times the sum of a and b is in a range of from about 0.7 to about 1.5; and the number-average molecular weight of the surfactant is in a range of from about 5,000 to about 35,000.

The present invention further provides a coated polymeric fabric which includes:

a base ply of a polymeric fabric having a surface; and a surfactant on the surface of the fabric;

in which the surfactant has a solubility in water at 20° C. no greater than about 5 percent by weight, based on the weight of the water, and is present on the fabric in an amount sufficient to durably render the polymeric fabric resistant to protein adsorption.

The present invention additionally provides a coated polymeric fabric which includes:

a base ply of a polymeric fabric having a surface; and a surfactant on the surface of the fabric;

in which the surfactant has a solubility in water at 20° C. no greater than about 5 percent by weight, based on the weight of the water, is present on the fabric in an amount sufficient to durably render the polymeric fabric resistant to protein adsorption, and has the general formula given above.

The present invention still further provides a disposable absorbent article, at least one component of which is the coated polymeric fabric of the present invention. More generally, the present invention provides a disposable absorbent article, at least one component of which is resistant to protein adsorption. Examples of disposable absorbent articles include diapers, feminine care products, such as sanitary napkins and tampons, incontinent care products, training pants, wipes, and the like.

DETAILED DESCRIPTION OF THE INVENTION

Figure 1:
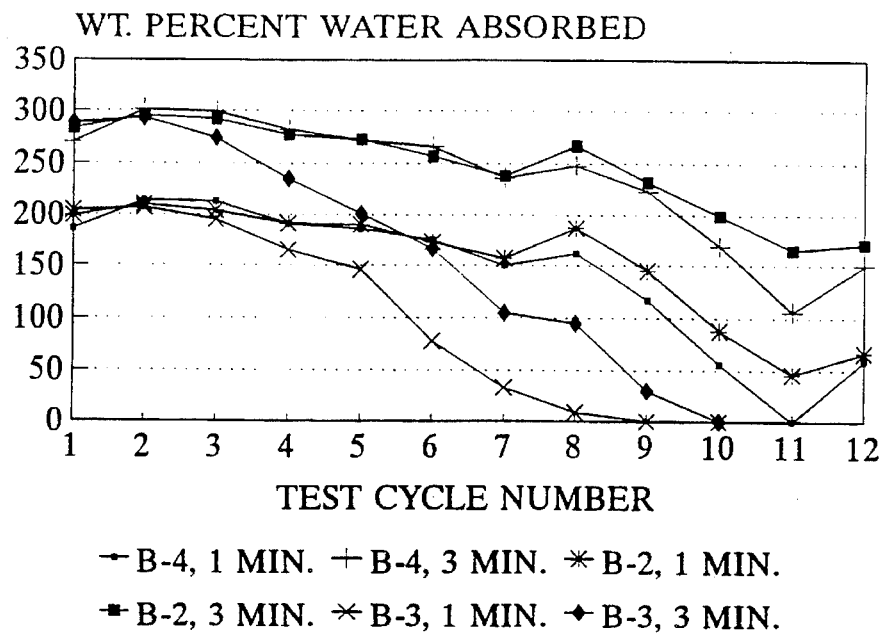
FIGS. 1–4, inclusive, are plots of test cycle number versus weight percent water absorbed by a polymeric fabric to which a surfactant has been applied in accordance with the present invention.

The term "protein" is meant to include any protein, including both simple proteins and such conjugated proteins as, by way of example only, nucleoproteins, lipoproteins, glycoproteins, phosphoproteins, hemoproteins, flavoproteins, and metalloproteins. Thus, the term is meant to encompass, without limitation, enzymes, storage proteins, transport proteins, contractile proteins, protective proteins, toxins, hormones, and structural proteins, by way of illustration only. In addition, the term includes a single protein and a mixture of two or more proteins.

As used herein, the term "polymeric fabric" means a fabric prepared from any polymeric material capable of being formed into a fabric. Thus, such material can be synthetic or natural, although the former are more likely to be employed in the present invention. Examples of natural polymeric materials include, cotton, silk, wool, and cellulose, by way of illustration only.

Synthetic polymeric materials, in turn, can be either thermosetting or thermoplastic materials, with thermoplastic materials being more common. Examples of thermosetting polymers include, by way of illustration only, alkyd resins, such as phthalic anhydride-glycerol resins, maleic acid-glycerol resins, adipic acid-glycerol resins, and phthalic anhydride-pentaerythritol resins; allylic resins, in which such monomers as diallyl phthalate, diallyl isophthalate diallyl maleate, and diallyl chlorendate serve as nonvolatile cross-linking agents in polyester compounds; amino resins, such as aniline-formaldehyde resins, ethylene urea-formaldehyde resins, dicyandiamide-formaldehyde resins, reelamine-formaldehyde resins, sulfonamide-formaldehyde resins, and urea-formaldehyde resins; epoxy resins, such as cross-linked epichlorohydrin-bisphenol A resins; phenolic resins, such as phenol-formaldehyde resins, including Novolacs and resols; and thermosetting polyesters, silicones, and urethanes.

Examples of thermoplastic polymers include, by way of illustration only, end-capped polyacetals, such as poly(oxymethylene) or polyformaldehyde, poly(trichloroacetaldehyde), poly(n-valeraldehyde), poly(acetaldehyde), poly(propionaldehyde), and the like; acrylic polymers, such as polyacrylamide, poly(acrylic acid), poly(methacrylic acid), poly(ethyl acrylate), poly(methyl methacrylate), and the like; fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), poly(vinyl fluoride), and the like; polyamides, such as poly(6-aminocaproic acid) or poly(ε-caprolactam), poly(hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly(sulfonyl-1,4-phenyleneoxy-1,4-phenylenesulfonyl-4,4'-biphenylene), and the like; polycarbonates, such as poly(bisphenol A)or-poly(carbonyldioxy-1,4-phenyleneisopropylidene-1,4-phenylene), and the like; polyesters, such as poly(ethylene terephthalate), poly(tetramethylene terephthalate), poly(cyclohexylene- 1,4-dimethylene terephthalate) or poly(oxymethylene-1,4-cyclohexylenemethyleneoxyterephthaloyl), and the like; polyaryl sulfides, such as poly(p-phenylene sulfide) or poly(thio-1,4-phenylene), and the like; polyimides, such as poly(pyromellitimido-1,4phenylene), and the like; polyolefins, such as polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly- 1,3-butadiene, polyisoprene, polychloroprene, polyacrylonitrile, poly(vinyl acetate), poly(vinylidene chloride), polystyrene, and the like; copolymers of the foregoing, such as acrylonitrile-butadiene-styrene (ABS) copolymers, and the like; and the like. In certain embodiments, the polymeric fabric will be prepared from a polyolefin. In other embodiments, the polyolefin will be polypropylene.

The term "fabric" is used broadly herein to mean any fibrous material which has been formed into a sheet or web. That is, the fabric is composed, at least in pan, of fibers of any length. Thus, the fabric can be a woven or nonwoven sheet or web, all of which are readily prepared by methods well-known to those having ordinary skill in the art. For example, nonwoven webs are prepared by such processes as meltblowing, coforming, spunbonding, carding, air laying, and wet laying. Moreover, the fabric can consist of a single layer or multiple layers. In addition, a multilayered fabric can include films, scrim, and other nonfibrous materials.

As used herein, the term "durable" means that the polymeric fabric to which a surfactant has been applied can be subjected to the rigorous washing procedure described hereinafter or to multiple exposures to water and remain both wettable and resistant to protein adsorption.

The term "surfactant" is used herein to mean any surface-active agent which is capable of durably rendering a polymeric fabric wettable and/or resistant to protein adsorption. On occasion, resistance to protein adsorption is referred to herein as a reduced tendency to adsorb protein or as protein antifouling characteristics. The surfactant has a solubility in water at 20° C. no greater than about 5 percent by weight, based on the weight of the water. In some embodiments, the surfactant is a linear polysiloxane which is terminated at each end by a polyether moiety, commonly referred to as an A-B-A polymer. In other embodiments, the surfactant is a polysiloxane polyether having the general formula,

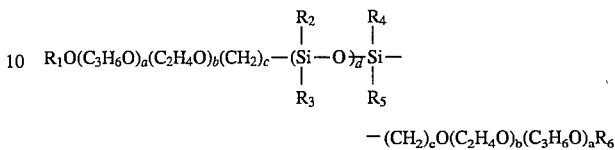

$$-(CH_2)_cO(C_2H_4O)_b(C_3H_6O)_aR_6$$

wherein:

each of $R_1$ and $R_6$ independently is selected from the group consisting of hydrogen and $C_1$–$C_8$ alkyl and aryl groups;

each of $R_2$–$R_5$ independently is selected from the group consisting of $C_1$–$C_8$ alkyl and aryl groups;

a represents an integer from about 8 to about 25;

b represents an integer from about 8 to about 25;

the ratio of b to a is in a range of from about 0.7 to about 1.5;

c represents an integer from 1 to about 10;

d represents an integer from about 40 to about 100;

the ratio of d to two times the sum of a and b is in a range of from about 0.7 to about 1.5; and the number-average molecular weight of the surfactant is in a range of from about 5,000 to about 35,000.

In still other embodiments, with reference to the foregoing general formula, each of $R_1$ and $R_6$ independently is selected from the group consisting of hydrogen and $C_1$–$C_3$ alkyl and phenyl groups;

each of $R_2$–$R_5$ independently is selected from the group consisting of $C_1$–$C_3$ alkyl and phenyl groups;

a represents an integer from about 12 to about 18;

b represents an integer from about 12 to about 18;

the ratio of b to a is about 1;

c represents an integer from about 2 to about 4;

d represents an integer from about 50 to about 70;

the ratio of d to two times the sum of a and b is about 1; and the number-average molecular weight of the surfactant is in a range of from about 6,500 to about 18,500.

In yet other embodiments, again with reference to the foregoing general formula, each of $R_1$ and $R_6$ is hydrogen;

each of $R_2$–$R_5$ is a methyl group;

a represents an integer which is about 15;

b represents an integer which is about 15;

c represents an integer which is 3;

d represents an integer which is about 60; and the number-average molecular weight of the surfactant is about 7,000.

While the composition which is applied to the polymeric fabric is described in terms of water and a surfactant, it should be apparent to those having ordinary skill in the art that the term "surfactant" is meant to include both a single surfactant and a mixture of two or more surfactants as defined above. Thus, the term "composition" is used herein to mean a mixture (e.g., a solution or a dispersion) of one or more surfactants in water. The composition sometimes is referred to herein as the "surfactant composition."

A method of the present invention is directed to durably rendering a polymeric fabric resistant to protein adsorption. Such method involves providing a polymeric fabric having a surface, applying to the surface of the polymeric fabric a composition which includes water and a surfactant adapted to durably render the polymeric fabric resistant to protein adsorption, and drying the polymeric fabric. In general, the surfactant is present on the polymeric fabric in an amount sufficient to durably render the polymeric fabric resistant to protein adsorption and has a solubility in water at 20° C. no greater than about 5 percent by weight, based on the weight of the water.

A method of the present invention also is directed to durably rendering a polymeric fabric wettable and resistant to protein adsorption. Such method involves providing a polymeric fabric having a surface, applying to the surface of the polymeric fabric a composition which includes water and a surfactant having the general formula presented earlier, and drying the polymeric fabric. Again, the surfactant is present on the polymeric fabric in an amount sufficient to durably render the polymeric fabric wettable and resistant to protein adsorption and has a solubility in water at 20° C. no greater than about 5 percent by weight, based on the weight of the water.

In either method, a polymeric fabric as already defined is provided. To the fabric then is applied in the second step a composition which includes water and a surfactant as already defined. The level of the surfactant in the composition can vary over a wide range. In general, the level of the surfactant is a function of the amount of the surfactant which is desired to be added to the polymeric fabric. As a practical matter, the level of the surfactant in the composition typically will be in a range of from about 0.1 to about 3 percent by weight, based on the weight of water. Depending on the level of add-on desired, however, lower or higher levels can be employed. As used herein, the term "add-on" refers to the weight percent of surfactant on a dry weight basis which is present on the polymeric fabric.

The composition which includes water and a surfactant can be applied to a surface of the polymeric fabric by any means known to those having ordinary skill in the art. Such means include, by way of illustration only, dipping, doctor blading, spraying, and direct and offset gravure printing or coating.

Drying of the treated polymeric fabric also can be accomplished by any known means. Examples of known drying means include, by way of illustration only, convection ovens, radiant heat, infrared radiation, forced air ovens, and heated rolls or cans. Drying also includes air drying without the addition of heat energy, other than that present in the ambient environment.

The coated polymeric fabric which is obtained after the drying step has two significantly improved characteristics. First, the fabric is wettable. Second, the fabric is resistant to protein adsorption; i.e., it exhibits a reduced tendency to adsorb protein, compared with the identical fabric which has not been coated with the surfactant. Moreover, these two characteristics are durable as defined herein.

The amount of surfactant present on the polymeric fabric in general will be at least about 0.3 percent by weight, based on the weight of the polymeric fabric. As a practical matter, the amount of surfactant present typically will be in a range of from about 0.3 to about 10 percent by weight. In certain embodiments, the amount of surfactant present on the fabric will be in a range of from about 0.5 to about 7 percent by weight. In other embodiments, the amount of surfactant present on the fabric will be in a range of from about 0.5 to about 3 percent by weight.

The coated polymeric fabric of the present invention is suitable as a component of a disposable absorbent article. Typical absorbent articles, include, by way of illustration only, diapers; feminine care products, such as sanitary napkins and tampons; incontinent products; training pants; and wipes.

The present invention is further described by the examples which follow. Such examples, however, are not to be construed as limiting in any way either the spirit or the scope of the present invention. In the examples, all parts are by weight, unless stated otherwise.

EXAMPLE 1

Demonstration of Wettability

The polymeric fabric used in this example was a standard Kimtex® wipe (Kimberly-Clark Corporation, Roswell, Ga.). The wipe was a meltblown polypropylene nonwoven web having a basis weight of 2.0 ounces per square yard (osy, equivalent to about 47 grams per square meter, $g/m^2$). It was thermally point-bonded in a woven web pattern, with the bond points constituting about 17 percent of the total wipe area. In all cases, 3-inch×8-inch (about 7.6cm×20.3-cm) samples of wipe were employed.

The surfactant utilized was a linear polysiloxane polyether having the following structural formula:

$$HO(C_3H_6O)_{15}(C_2H_4O)_{15}(CH_2)_3-(\underset{\underset{CH_3}{|}}{\overset{\overset{CH_3}{|}}{Si}}-O-)_{60}-\underset{\underset{CH_3}{|}}{\overset{\overset{CH_3}{|}}{Si}}-(CH_2)_3O(C_2H_4O)_{15}(C_3H_6O)_{15}H$$

The surfactant had a number-average molecular weight of about 6,000, a weight-average molecular weight of about 11,100, and a z-average molecular weight of about 16,000. The polydispersity of the surfactant was 1.85. It will be referred to hereinafter as Surfactant A.

Four compositions of deionized water and the surfactant were prepared and identified as Compositions A-D, inclusive. The concentrations of surfactant in the compositions were 0.1, 0.5, 1.0, and 3.0 percent by weight, respectively. The two lower concentrations formed clear solutions, while the two higher concentrations formed stable emulsions.

Four samples were prepared with each concentration. Each sample of wipe was weighed and allowed to soak in 500 ml of the surfactant composition for five minutes at ambient temperature. The soaked sample was removed from the surfactant composition, passed through an Atlas Laboratory Wringer having a 30-lb (13 .6-kg) nip setting (Atlas Electric Devices Company, Chicago, Ill.), and allowed to air dry in a fume hood overnight. The sample then was weighed and the add-on of surfactant calculated as a percentage based on the original dry weight of the sample as follows:

Percent add-on=100×(g TPF−g PF)/g PF wherein "g TPF" refers to the dry weight of the polymeric fabric to which the surfactant composition has been applied and "g PF" refers to the dry weight of the original fabric sample. The results are summarized in Table 1 which includes the mean percent add-on and standard deviation for each composition. For convenience, samples to which a surfactant composition was applied were labeled with the letter of the composition, followed by the number of the sample. Thus, the samples treated with Composition A were identified as Samples A-1 through A-4, inclusive, and so on.

TABLE 1

Percent Add-On Values for Samples A–D

| Sample | g TPF | g PF | Difference | % Add-on | Mean Value |
|---|---|---|---|---|---|
| A-1 | 0.9562 | 0.9551 | 0.0011 | 0.115 | — |
| A-2 | 1.0229 | 1.0216 | 0.0013 | 0.127 | — |
| A-3 | 0.9129 | 0.9122 | 0.0007 | 0.077 | — |
| A-4 | 0.9906 | 0.9895 | 0.0011 | 0.111 | 0.108 ± 0.021 |
| B-1 | 0.9704 | 0.9604 | 0.0100 | 1.041 | — |
| B-2 | 0.9550 | 0.9456 | 0.0094 | 0.994 | — |
| B-3 | 0.9637 | 0.9522 | 0.0115 | 1.208 | — |
| B-4 | 0.9981 | 0.9886 | 0.0095 | 0.961 | 1.051 ± 0.110 |
| C-1 | 1.0572 | 1.0303 | 0.0269 | 2.611 | — |
| C-2 | 1.0158 | 0.9978 | 0.0180 | 1.804 | — |
| C-3 | 1.0332 | 1.0176 | 0.0156 | 1.533 | — |
| C-4 | 0.9800 | 0.9651 | 0.0149 | 1.544 | 1.873 ± 0.508 |
| D-1 | 1.0502 | 0.9807 | 0.0695 | 7.087 | — |
| D-2 | 1.0414 | 0.9696 | 0.0718 | 7.405 | — |
| D-3 | 1.0585 | 0.9861 | 0.0724 | 7.342 | — |
| D-4 | 1.0604 | 0.9861 | 0.0743 | 7.535 | 7.342 ± 0.188 |

Many of the samples listed in Table 1 were subjected to the Water Absorbency Test A described in U.S. Pat. No. 5,102,738 to Bell et al., which patent is incorporated herein by reference. The test was repeated for 12 cycles or until the sample no longer absorbed water. In some cases, the sample was removed from the test apparatus and simply allowed to air-dry. In other cases, the sample was passed through an Atlas Laboratory Wringer (nipped) as already described, then allowed to air-dry. None of Samples A-1 through A-4 could be subjected to the test as they were not wettable by water. The amount of water absorbed by each sample after one minute and three minutes was recorded in each case. The data are summarized in Tables 2–4, inclusive.

TABLE 2

Summary of Test Results for Samples B-2, B-3, and B-4
Water Absorbed as Percent of Sample Weight

| | Sample B-4 | | Sample B-2 | | Sample B-3[a] | |
|---|---|---|---|---|---|---|
| Cycle | 1 Min. | 3 Min. | 1 Min. | 3 Min. | 1 Min. | 3 Min. |
| 1 | 186 | 270 | 199 | 283 | 204 | 288 |
| 2 | 214 | 301 | 210 | 295 | 207 | 293 |
| 3 | 213 | 299 | 204 | 292 | 195 | 274 |
| 4 | 191 | 282 | 191 | 277 | 165 | 235 |
| 5 | 186 | 272 | 190 | 273 | 146 | 201 |
| 6 | 175 | 266 | 173[b] | 257[b] | 78[b] | 166[b] |
| 7 | 150[b] | 236[b] | 157 | 238 | 33 | 105 |
| 8 | 162 | 248 | 187 | 267 | 9 | 95 |
| 9 | 117 | 223 | 145 | 232 | 0 | 30 |
| 10 | 56 | 169 | 88 | 199 | 0 | 0 |
| 11 | 0 | 106 | 46 | 165 | — | — |
| 12 | 59 | 150 | 67 | 171 | — | — |

[a]Sample nipped after each test cycle.
[b]The fabric did not wet instantly in this and subsequent cycles.

TABLE 3

Summary of Test Results for Samples C-2, C-1, and C-3
Water Absorbed as Percent of Sample Weight

| | Sample C-2 | | Sample C-1[a] | | Sample C-3[a] | |
|---|---|---|---|---|---|---|
| Cycle | 1 Min. | 3 Min. | 1 Min. | 3 Min. | 1 Min. | 3 Min. |
| 1 | 196 | 280 | 190 | 274 | 194 | 280 |
| 2 | 203 | 280 | 203 | 278 | 199 | 275 |
| 3 | 213 | 292 | 203 | 270 | 191 | 265 |
| 4 | 192 | 267 | 175 | 235 | 164 | 235 |
| 5 | 197 | 272 | 167 | 225 | 153[b] | 229[b] |
| 6 | 194 | 271 | 178 | 252 | 115 | 202 |
| 7 | 172[b] | 254[b] | 118[b] | 218[b] | 0 | 168 |
| 8 | 170 | 244 | 2 | 168 | 0 | 138 |
| 9 | 165 | 254 | 0 | 45 | 0 | 125 |
| 10 | 145 | 249 | 0 | 21 | 0 | 0 |
| 11 | 138 | 238 | — | — | — | — |
| 12 | 130 | 231 | — | — | — | — |

[a]Sample nipped after each test cycle.
[b]The fabric did not wet instantly in this and subsequent cycles.

TABLE 4

Summary of Test Results for Samples D4, D-2, D-3, and D-1
Water Absorbed as Percent of Sample Weight

| | Sample D-4 | | Sample D-2 | | Sample D-3[a] | | Sample D-1[a] | |
|---|---|---|---|---|---|---|---|---|
| Cycle | 1 Min. | 3 Min. | 1 Min. | 3 Min. | 1 Min. | 3 Min. | 1 Min. | 3 Min. |
| 1 | 198 | 258 | 193 | 253 | 186 | 240 | 204 | 265 |
| 2 | 167 | 222 | 163 | 217 | 159 | 204 | 153 | 200 |
| 3 | 159 | 214 | 170 | 226 | 150 | 194 | 136 | 183 |
| 4 | 152 | 192 | 164 | 212 | 134 | 171 | 129 | 168 |
| 5 | 142 | 180 | 156 | 199 | 152 | 192 | 139 | 174 |
| 6 | 150 | 194 | 156 | 197 | 157 | 193 | 150 | 181 |
| 7 | 141 | 169 | 158 | 187 | 154 | 188 | 145 | 168 |
| 8 | 186 | 228 | 162 | 190 | 125 | 142 | 145 | 171 |
| 9 | 162 | 195 | 155 | 187 | 155 | 182 | 131 | 156 |
| 10 | 146 | 168 | 151 | 174 | 128[b] | 150[b] | 123[b] | 150[b] |
| 11 | 155 | 183 | 162 | 190 | 123 | 150 | 132 | 166 |
| 12 | 144 | 173 | 150 | 178 | 133 | 159 | 139 | 169 |

[a]Sample nipped after each test cycle.
[b]The fabric did not wet instantly in this and subsequent cycles.

Figure 2:
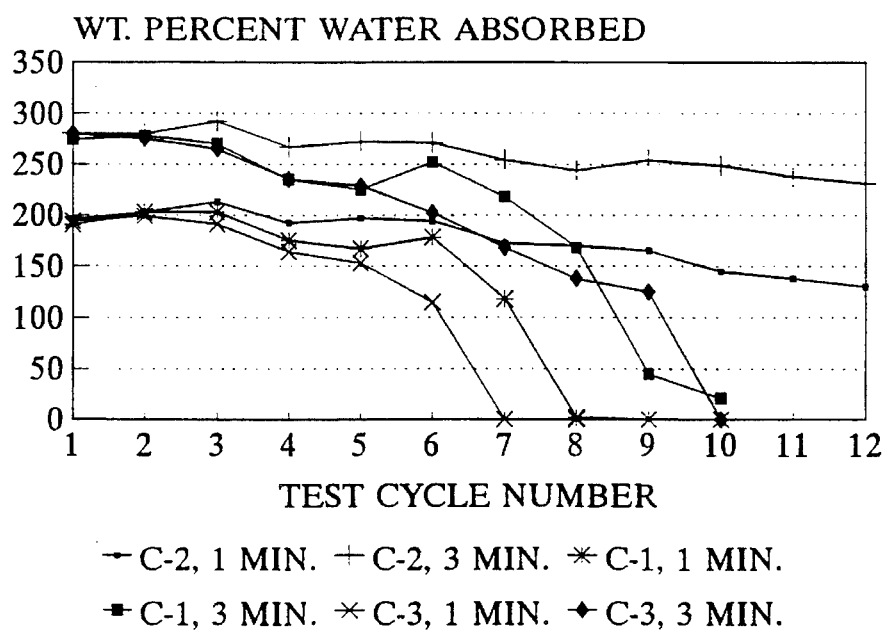
Figure 3:
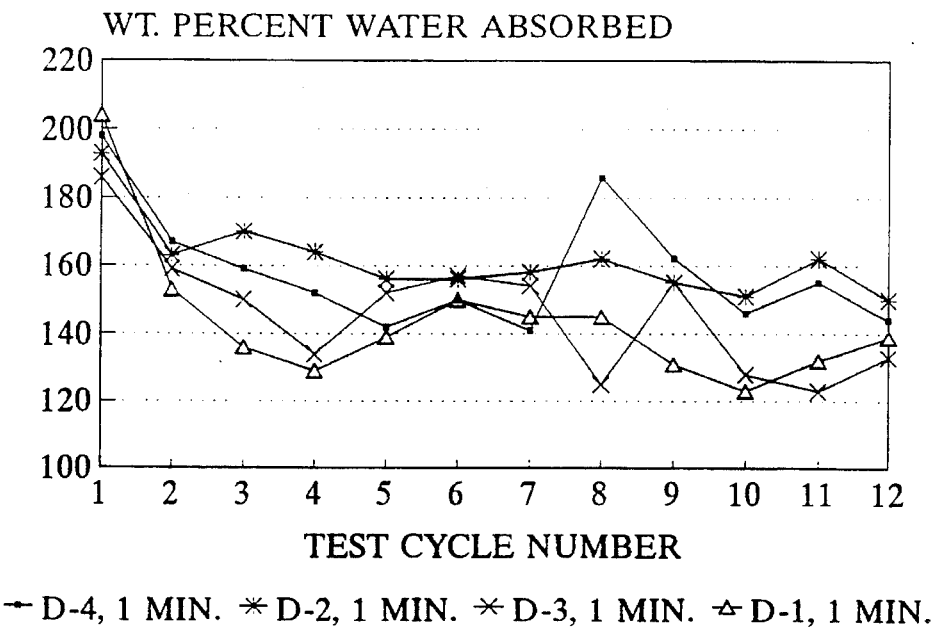
Figure 4:
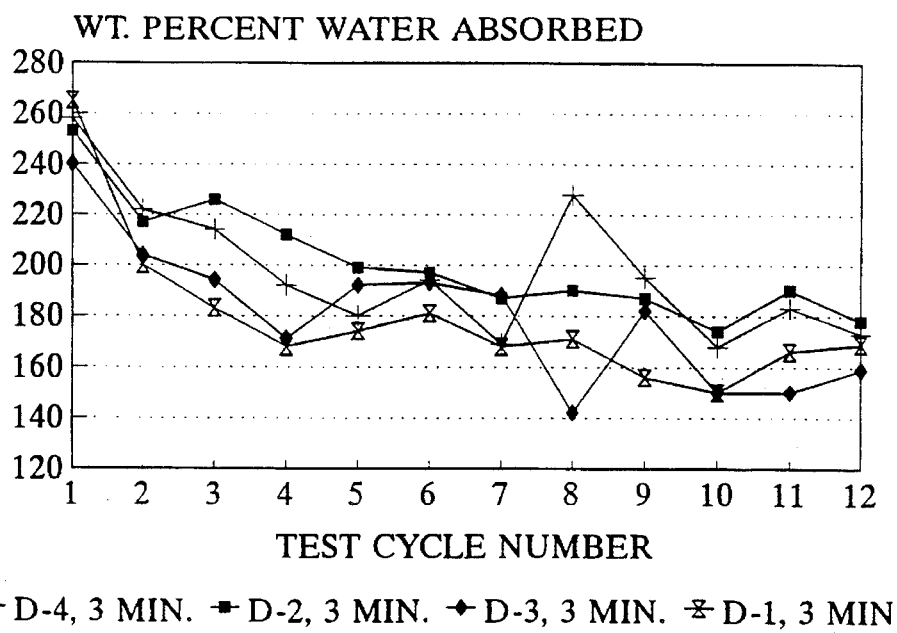

In order to better understand the data in the Table 2, such data were plotted as test cycle number versus the weight percent of water absorbed by the sample. The resulting plot is shown in FIG. 1. A similar plot was prepared for the data in Table 3 and is shown in FIGS. 2. The data in Table 4 were separated for plotting, based on the time period. Thus, the data for 1 minute were plotted together, shown in FIG. 3, and the data for 3 minutes were plotted together, shown in FIG. 4. For convenience in viewing the plots in FIGS. 3 and 4, the y-axis values were narrowed to cover only the range of the plots, rather than beginning with zero water absorbed.

The data in the tables, emphasized by the figures, makes it clear that Surfactant A durably renders the polymeric fabric wettable. Interestingly, the maximum amount of water absorbed by a sample after three minutes appears to be inversely proportional to the amount of surfactant on the fabric. However, the durability of the coating of surfactant on the sample is proportional to the amount of surfactant which is initially present. Durability is increased when the sample is not nipped between test cycles. The differences between nipped samples and samples which were not nipped are almost negligible at the highest add-on tested.

EXAMPLE 2

Demonstration of Protein Antifouling Properties (Protein Detection by ELISA)

An enzyme-linked immunosorbent assay (ELISA) typically is used to detect antigens or antibodies in small volumes of liquids. The assay was adapted to detect the presence of an antigen (i.e., a protein) on a polymeric nonwoven fabric. The assay is based on the specificity of the reaction between the antigen and an antibody which is specific for the antigen. The antibody bears a conjugated enzyme which permits the colorimetric detection of the presence of the antibody when exposed to a suitable reagent. There are six basic steps to the ELISA: (1) exposure of the nonwoven fabric to the antigen, (2) addition of an inert protein to prevent background interference, (3) exposure of the nonwoven fabric to enzyme-conjugated antibody to permit specific binding of the antibody with antigen which may be present on the fabric, (4) removal of unbound antibody, (5) addition of a reagent which is specific for the conjugated enzyme and which develops a color in the presence of the enzyme, and (6) determining the amount of antigen present on the fabric from the color resulting from the reaction of the conjugated enzyme with the reagent.

A human albumin (Protein A) solution was prepared by stirring for 30 minutes a mixture of 0.05 g human albumin (Sigma A9511, Lot 127F9320, Sigma Chemical Company, St. Louis, Mo.), 0.71 g dibasic sodium phosphate, and 250 ml Milli-Q deionized water. A human fibrinogen (Protein F) solution was similarly prepared from a mixture of 0.007 g human fibrinogen (Sigma F4883, Lot 72H9320), 0.099 g dibasic sodium hydroxide, and 35 ml Milli-Q deionized water.

Three different polymeric fabrics were employed. The first, Fabric A, was a polypropylene spunbonded web having a basis weight of 0.8 osy (19 g/m$^2$). The fabric was produced as described in U.S. Pat. No. 3,341,394 to Kinney. The second fabric, Fabric B, also was a polypropylene spunbonded web having a basis weight of 0.8 osy (19 g/m$^2$). The material was produced as described in U.S. Pat. No. 3,802,817 to Matsuki et al. The third, Fabric C, was a spunbonded web comprised of polyethylene-polypropylene side-by-side bicomponent, 3-denier fibers. The fabric also had a basis weight 0.8 osy (19 g/m$^2$) and was produced as described in copending and commonly assigned Application Ser. No. 07/933,444, filed Aug. 21, 1992, now U.S. Pat. No. 5,382,400.

Several different surfactants were studied. Surfactant A was the surfactant employed in Example 1. Surfactant B was a polyethoxylated octylphenol, Triton® X-102 (Rohm and Haas Co., Philadelphia, Pa.). Surfactant C also was a polyethoxylated octylphenol, Triton®X-100 (Rohm and Haas Co.), similar to Triton® X-102.

Surfactant was applied to a piece of nonwoven fabric which was 6 inches×10 inches (about 15 cm×25 cm). The fabric was placed in about 650 ml of surfactant composition for one minute. The fabric then was removed from the surfactant composition and passed through an Atlas Laboratory Wringer having a 30-lb (13.6-kg) nip setting. The fabric was allowed to air dry in a fume hood.

Control samples consisted of fabric to which surfactant had not been applied.

The samples are summarized in Table 5.

TABLE 5

Summary of Samples for Protein Antifouling Studies

| Sample | Fabric | Surfactant Type | Concn.[a] | % Add-on[b] |
|---|---|---|---|---|
| A | A | — | — | — |
| B | A | A | 1.0 | 4.6 |
| C | A | B | 0.3 | 1.4 |
| D | B | — | — | — |
| E | B | A | 0.25 | 1.0 ± 0.2 |
| F | B | C | 0.25 | 0.9 ± 0.1 |
| G | C | — | — | — |
| H | C | A | 0.25 | 1.5 ± 0.5 |
| I | C | B | — | 0.27 |

[a]Percent by weight, based on the weight of the water.
[b]Percent by weight, based on the dry weight of the fabric.

Fabric samples were cut into 1-cm×5-cm strips and placed in borosilicate glass test tubes, one strip per tube. Except for controls, each fabric was exposed in the test tubes to 10 ml of the Protein A solution or 5 ml of the Protein F solution for 2.5 hours at ambient temperature. Care was taken to assure that the sample was completely immersed in each and all subsequent solutions. The protein solution was removed and to each tube was added 5 ml of a 1:10 dilution of bovine serum albumin diluent/blocking solution concentrate (Kirkegaard and Perry Laboratories or KPL, Gaithersburg, Md.). The tubes then were allowed to stand for 1.5 hours at ambient temperature.

The bovine serum albumin diluent/blocking solution was removed from each tube and replaced with a diluted solution of anti-human albumin antibody with peroxidase conjugate (The Binding Site, PP032, Lot G3406) or anti-human fibrinogen antibody with peroxidase conjugate (The Binding Site, PP056, Lot G23537B), as appropriate. After being allowed to stand at ambient temperature for about 1 hour, the samples were removed from the test tubes and replicate samples were combined in beakers. The samples were soaked three times for about 30 minutes per soaking with 20-ml portions of a 1:20 dilution of KPL Wash solution. Each soak solution was checked for conjugated enzyme activity; no activity was found in the last soak solution. The samples then were placed individually in clean borosilicate glass test tubes, covered with aluminum foil, and allowed to stand overnight at ambient temperature.

The enzyme reagent solution was prepared by mixing 12 1-mg tablets of tetramethylbenzidine (Sigma T3405), 250 µl of 3 percent hydrogen peroxide, and 125 ml of pH 5.05 phosphate-citrate buffer. Four ml of this solution was added to each test tube and the samples were allowed to stand for 20 minutes at ambient temperature with slight agitation. The samples then were removed from the test tubes and placed in clean tubes. The enzyme substrate solution remaining in the test tubes had developed a blue color, the intensity of which was proportional to the amount of protein adsorbed by the fabric. The absorbance of each enzyme substrate solution was measured at 650 nm in a Varian 2200 UV-visible spectrophotometer. The results are summarized in Table 6.

TABLE 6

Summary of ELISA Results

| Test No. | Sample | Protein Present | Type | Absorbance[a] |
|---|---|---|---|---|
| 1 | A | No | — | 0.25 |
| 2 | A | Yes | F | 0.93 ± 0.14 |
| 3 | B | No | — | 0.02 |
| 4 | B | Yes | F | 0.22 + 0.08 |
| 5 | C | No | — | 0.20 |
| 6 | C | Yes | F | 0.88 ± 0.08 |
| 7 | D | No | — | 0.21 ± 0.01 |
| 8 | D | Yes | F | 1.69 ± 0.55 |
| 9 | E | Yes | F | 0.67 + 0.32 |
| 10 | F | Yes | F | 1.03 ± 0.13 |
| 11 | D | No | — | 0.32 ± 0.03 |
| 12 | D | Yes | A | 0.91 ± 0.21 |
| 13 | E | Yes | A | 0.24 ± 0.03 |
| 14 | F | Yes | A | 1.02 ± 0.07 |
| 15 | G | No | — | 0.66 |
| 16 | G | Yes | A | 1.50 ± 0.34 |
| 17 | H | No | — | 0.14 |
| 18 | H | Yes | A | 0.50 ± 0.07 |
| 19 | I | No | — | 0.32 |
| 20 | I | Yes | A | 1.86 ± 0.57 |

[a]When replicate samples were tested, the absorbance value is the mean value ± the standard deviation.

The data in Tables 5 and 6 demonstrate the effectiveness of a defined surfactant for reducing the adsorption of protein by a polymeric fabric. This is true even though actual amounts of protein on the fabrics were not determined. Nevertheless, the absorbance values obtained clearly are proportional to the amount of protein adsorbed by the fabric.

Figure 5:
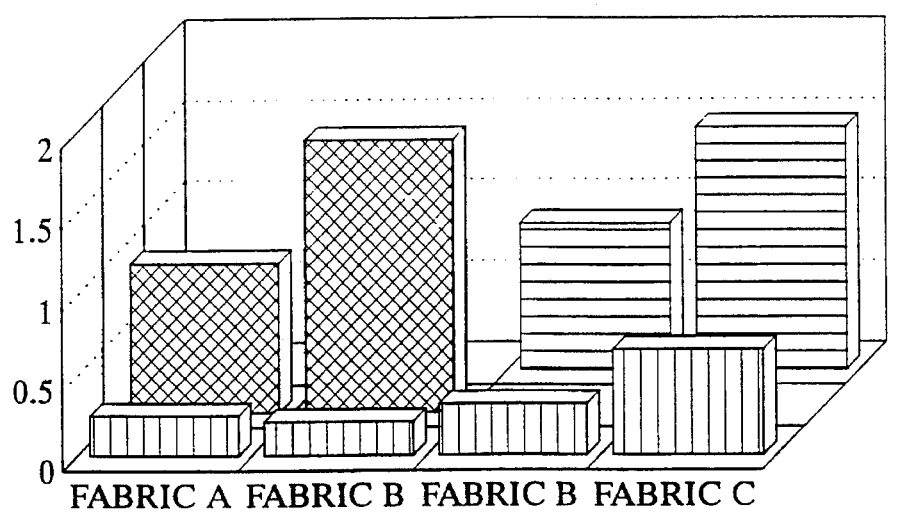
FIGS. 5–10 are three dimensional bar graphs showing absorbance values obtained by an ELISA for adsorbed protein for a number of different polymeric fabrics, to some of which surfactants have been applied.

In order to aid in the visualization of the data in Tables 5 and 6, three-dimensional bar graphs of fabric type/treatment versus absorbance were prepared. The first is a plot of the results of Test Numbers 1, 2, 7, 8, 11, 12, 15, and 16 from Table 6 and is shown in FIG. 5. Such test numbers are controls in that none of the fabrics were treated with a surfactant (in this and subsequent figures, the term "virgin fabric" refers to fabric to which a surfactant composition has not been applied and which has not been intentionally exposed to a protein solution). Fabric B has two entries in FIG. 5 because two separate tests with virgin fabric were conducted (one with Protein F and one with Protein A). The figure graphically illustrates the substantial increase in absorbance which results from the presence of adsorbed protein on the fabrics. Although the amount of protein adsorbed was not determined, as already noted, the ability of a given surfactant to reduce adsorption (i.e., produce a protein antifouling surface) will be proportional to the reduction of absorbance values to levels approaching those for virgin fabric.

Figure 6:
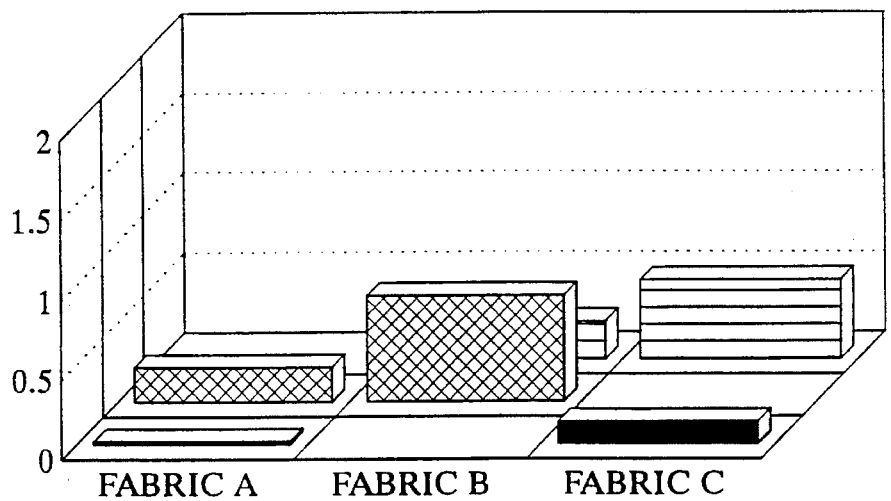
Figure 7:
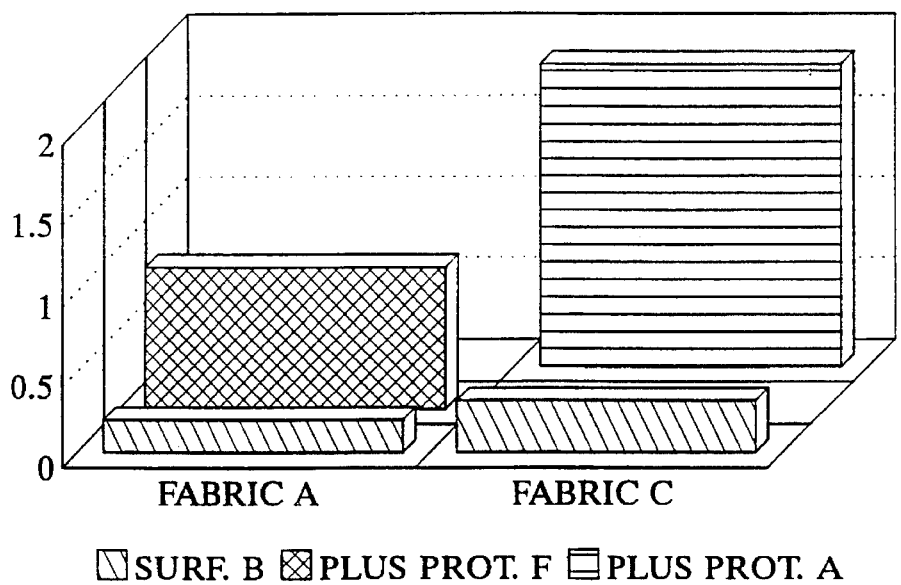

FIGS. 6 and 7 are similar to FIG. 5, except that the absorbance values are for fabric to which Surfactant A and Surfactant B, respectively, had been applied. Specifically, FIG. 6 is a plot of Test Numbers 3, 4, 9, 13, 17, and 18 from Table 6, and FIG. 7 is a plot of Test Numbers 5, 6, 19, and 20 from Table 6. FIG. 7 does not include Fabric B since the combination of Surfactant B with Fabric B was not studied. Note that FIGS. 5-7, inclusive, have the same y-axis scale, thereby permitting direct visual comparisons. The superiority of Surfactant A over Surfactant B is clearly evident.

Figure 8:
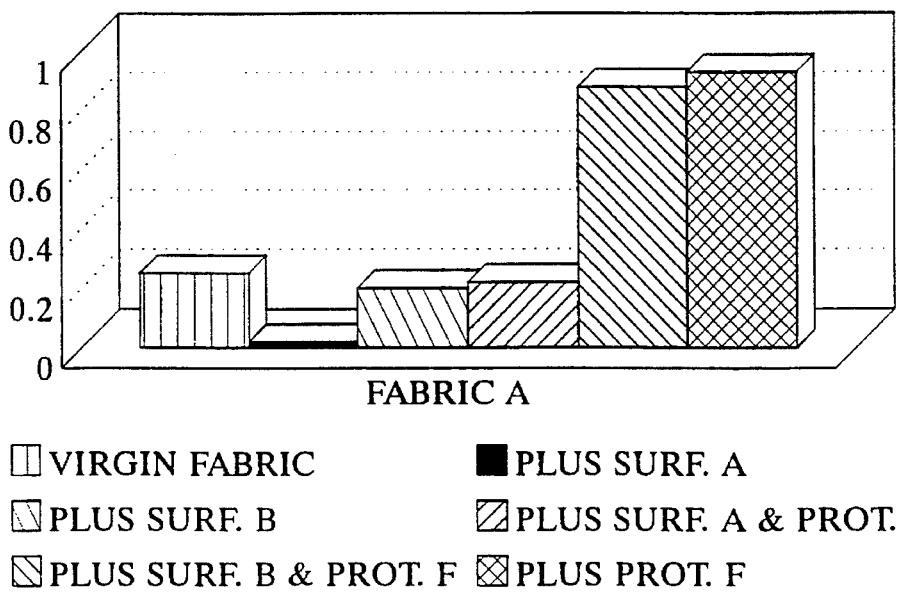
Figure 9:
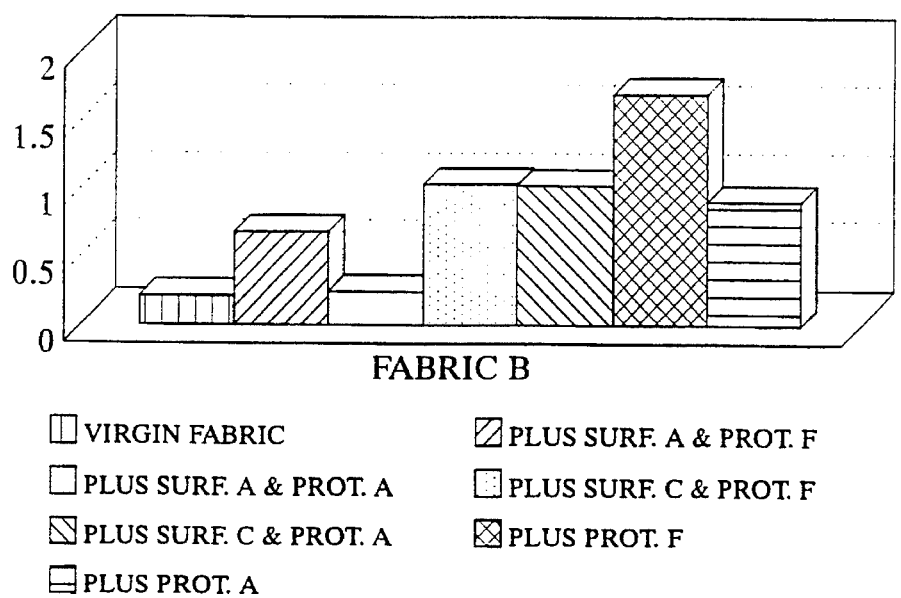
Figure 10:
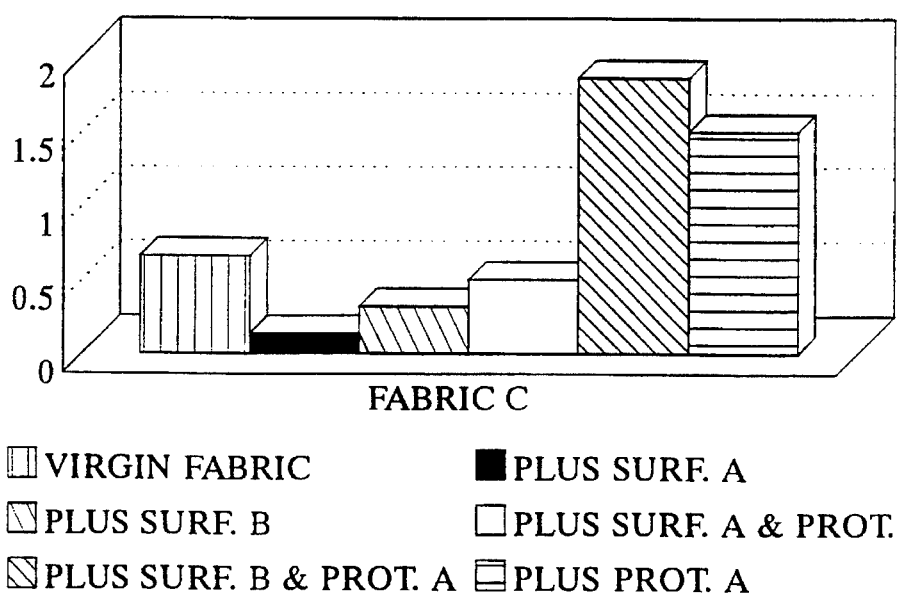

The efficacy of surfactants on Fabric A is shown in FIG. 8. The figure is similar to the preceding figures, except it is limited to Fabric A only. It permits a direct comparison of the efficacy of Surfactants A and B in reducing protein adsorption. Again, the superiority of Surfactant A is clear. Replacing the data for Fabric A with that for Fabric B resulted in FIG. 9. Although Surfactant A still is superior to Surfactant C, the differences are not as great as in FIG. 8. A similar plot for Fabric C was prepared and is shown in FIG. 10. Again, the superiority of Surfactant A is self-evident.

EXAMPLE 3

Demonstration of Durable Protein Antifouling Properties (Protein Detection by Radiolabeling)

The polymeric fabric employed in this example was a spunbonded polypropylene nonwoven web having a basis weight of 1.0 osy (about 24 g/m$^2$).

Three surfactants were employed. The first, Surfactant A, was the linear polysiloxane polyether of Example 1. The surfactant composition was prepared by mixing 20 g of the surfactant with 1,980 g of distilled water and stirring at ambient temperature for about 70 minutes.

The second surfactant, Surfactant D, was a polysiloxane polyether having the formula,

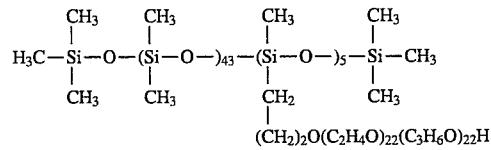

The material had a number-average molecular weight of 7,700, a weight-average molecular weight of 17,700, a z-average molecular weight of 27,700, and a polydispersity of 2.3. The surfactant composition was prepared by mixing 20 g of the surfactant with 1,980 g of distilled water and stirring at ambient temperature for about 70 minutes.

The third surfactant, Surfactant E, was similar to Surfactant D. The material had a number-average molecular weight of 13,000. The polyether side chains consisted of 77 percent by weight ethylene oxide and 23 percent by weight propylene oxide and the sum of ethylene oxide and propylene oxide repeating units was greater than 20. The material had a refractive index at 25° C. of 1.442, a specific gravity at 25° C. of 1.04 g/cm$^3$, and a viscosity at 25° C. of 10,000 centipoise. The surfactant composition was prepared by mixing 20 g of the surfactant with 1,980 g of distilled water and stirring at ambient temperature for about 4.5 hours.

A 7-inch x 7-inch (about 18-cm×18-cm) piece of the fabric was weighed and soaked in about 500–650 ml of the surfactant composition for about 10–12 minutes at ambient temperature. Two pieces of the fabric were soaked separately in each 500–650-ml portion of the composition. Each piece of fabric was removed from the composition and passed without folding through an Atlas Laboratory Wringer having a 40-lb (18.2-kg) nip setting. The piece of fabric was turned 90° and passed through the wringer a second time. The piece of fabric then was allowed to air dry in a fume hood overnight. The piece of fabric was weighed again. Surfactant A add-on was found to 3.08±0.31 percent by weight, based on the dry weight of the piece of fabric (Sample A). Add-on with Surfactants D and E was 3.17±0.35 and 3.08±0.44 percent by weight, respectively (Samples B and C, respectively). Sample D consisted of untreated fabric, i.e., fabric to which a surfactant had not been applied.

Before exposing samples to protein, the samples were subjected to a rigorous washing procedure. Specifically, each piece of treated fabric, i.e., fabric to which surfactant has been applied, was cut into approximately 11-mm×50-mm strips and placed in 10-ml test tubes, one strip per tube. Distilled water at ambient temperature was added to each tube to a level about 3 mm below the top of the tube. The strip of treated fabric was completely immersed below the level of the water. After no less than 30 minutes (typically after about 40 minutes), the water was removed from each tube by aspiration and replaced with fresh distilled water. After about two hours, the water again was removed from the test tube. The fabric strip in each tube then was rinsed three times by successively filling the tube with distilled water and removing the water by aspiration. The fabric strips were left in the test tubes in a fume hood and allowed to air dry. The level of Surfactant A remaining on each strip was found to be 1.07±0.10 percent by weight. The results for fabric strips treated with Surfactants D and E were 0.62±0.78 and 0.50±0.40, respectively.

The resulting samples were used for the fibrinogen protein adsorption experiments described below. The experiments were carded out in the laboratories of Dr. Allan S. Hoffman, Sc.D., Center for Bioengineering, University of Washington.

Fibrinogen from the baboon, Papio cynocephalus, was purified from citrated plasma supplied by the Regional Primate Research Center, University of Washington. Purification followed the poly(ethylene glycol)-β-alanine, fractionalprecipitation method developed for bovine fibrinogen by Weathersby et at. (*Thromb. Res.* 10:245–252, 1977), with the exception that aprotinin, an inhibitor of serine proteases (Pohl, *Methods Enzymol.* 182:68–83, 1990; Trasylol®, Mobay Chemical Company, New York, N.Y.), was added to the plasma at 40 Kunitz inhibitory units/ml (e.g., Horbert et al., *J. Biomed. Mater. Res.* 20:739–772, 1986; Bohnert et al., *J. Biomater. Sci. Polym. Ed.* 1:279–297, 1990; and Sheu, Unpublished Ph.D. dissertation, University of Washington, Seattle, 1992).

Except where noted otherwise, purified fibrinogen was dissolved in a pH 7.4 buffer comprising 0.01M sodium citrate to prevent clotting due to contaminating proteases, 0.01 M dibasic sodium phosphate, 0.12M sodium chloride, and 0.02 percent sodium azide as a bacteriostatic agent (Bohnert et al. 1990). This buffer will be referred to herein as cPBSz. During dialysis, presoaking, adsorption, displacement rinsing, and the final 24-hour soak-rinse, 0.01M sodium iodide was added to block sites for potential non-specific binding of iodide (Sheu 1992:66). This buffer is referred to herein as cPBSzI. To maintain a constant ionic strength, sodium chloride was reduced to 0.11M in cPBSzI.

The concentration of pooled fibrinogen was evaluated by spectrophotometry. Samples were diluted to approximately 0.3 to 0.5 mg/ml, and the concentration determined based on absorbance at 280 nm (Mihalyi, *Biochem.* 7:208–222, 1968).

Fibrinogen samples were iodinated by the iodine monochloride method, as modified by Horbett (*J. Biomed. Mater. Res.* 15:673–695, 1981) and Bergström et al. (*J. Biomed. Mater. Res.* 26:779–790, 1992). This method employed equimolar fibrinogen and iodine monochloride. As the reaction proceeded, $^{125}I$ was linked to the tyrosine residues in fibrinogen ortho to the phenolic hydroxy group.

The reaction mixture was then purified by size-exclusion chromatography on Biogel P4® (poly(acryamide-co-N,N'-methylene bisacrylamide); Bio-Rad laboratories, Richmond, Calif.). This gel filtration gave a good separation of bound and unbound iodine. The peak fractions (1.775 ml/fraction) of radiolabeled fibrinogen were pooled, then dialyzed extensively against cPBSzI using a cellulose-ester membrane (molecular-weight cutoff 12,000–14,000, Spectra/Por®). The retentate was aliquotted, frozen at −20° C., and used within one week.

All materials were studied in triplicate. The washed, treated 11-mm×50-mm strips were cut into 11-mm×15-mm rectangular samples. Samples were individually placed in polystyrene cups and soaked overnight in cPBSzI at 4° C. (Sheu 1992:42). Prior to use, the buffer was degasseal with a water-faucet aspirator (approximately 12–15 mm Hg) for at least 20 minutes, with stirring.

Following the overnight soak, the buffer was removed by aspiration and immediately replaced with 2.0 ml fresh, degassed cPBSzI. Protein was diluted in cPBSzI to a final concentration of 0.2 mg/ml. The mixture was spiked with $^{125}I$-fibrinogen to give a specific activity of 0.3 to 1×10$^6$ counts per minute per mg (cpm/mg).

Prior to the addition of the protein, samples were thermally equilibrated in a water bath at 37° C. for at least one hour. The protein solution also was equilibrated at 370C. Adsorption was initiated by adding 0.5 ml fibrinogen (1 mg/ml). The protein solution was mixed by gentle repipetting to prevent foaming. Samples were incubated for two hours at 37° C.

Adsorption was terminated by dilution/displacement rinsing with 25 volumes cPBSzI (100 ml) per sample. The dilution/displacement method avoids exposing the adsorbate to air (e.g., Bergström et al. 1992). To apply a consistent rinse, an automated system was developed in which a syringe pump (Model 4200-17, Harvard Apparatus, South Natick, Massachusetts) delivered a 20-ml burst at 200 ml/minute, followed by a one second pause, then a final 80-ml burst at 200 ml/minute. This two-step procedure also permitted the segregation of liquid radioactive wastes of differing specific activities.

Samples were placed in 2.0 ml cPBSzI in polystyrene scintillation vials and gamma counted (Gamma Trac 1185, TM Analytic). From these results, the initial adsorption was calculated as the mass per fabric area (μg fibrinogen adsorbed/3.3 cm$^2$). This calculation treats the samples as if they were smooth, planar surfaces, with a surface area of 2×1.1 cm×1.5 cm, or 3.3 cm$^2$.

After counting, samples were incubated in the cPBSzI for 24 hours ("soakrinse;" Sheu 1992:42). The next day, they were dip rinsed, placed in clean counting tubes, and counted again to give a retained protein value. The results are summarized in Table 7. The percent add-on shown in the table for each fabric was obtained with larger pieces of polymeric fabric which had been subjected to the wash procedure described above.

TABLE 7

Summary of Radiolabeling Results

| | Surfactant | | Nanograms Protein/3.3 cm$^2$ Fabric | |
|---|---|---|---|---|
| Sample | Type | % Add-on[a] | Initial Value | Final Value |
| A | A | 1.1 | 47 ± 23 | 41 ± 29 |
| B | D | 0.6 | 573 ± 175 | 355 ± 86 |
| C | E | 0.5 | 2372 ± 529 | 2212 ± 540 |
| D | — | — | 3433 ± 362 | 2673 ± 304 |

[a]Percent by weight, based on the dry weight of the fabric.

Figure 11:
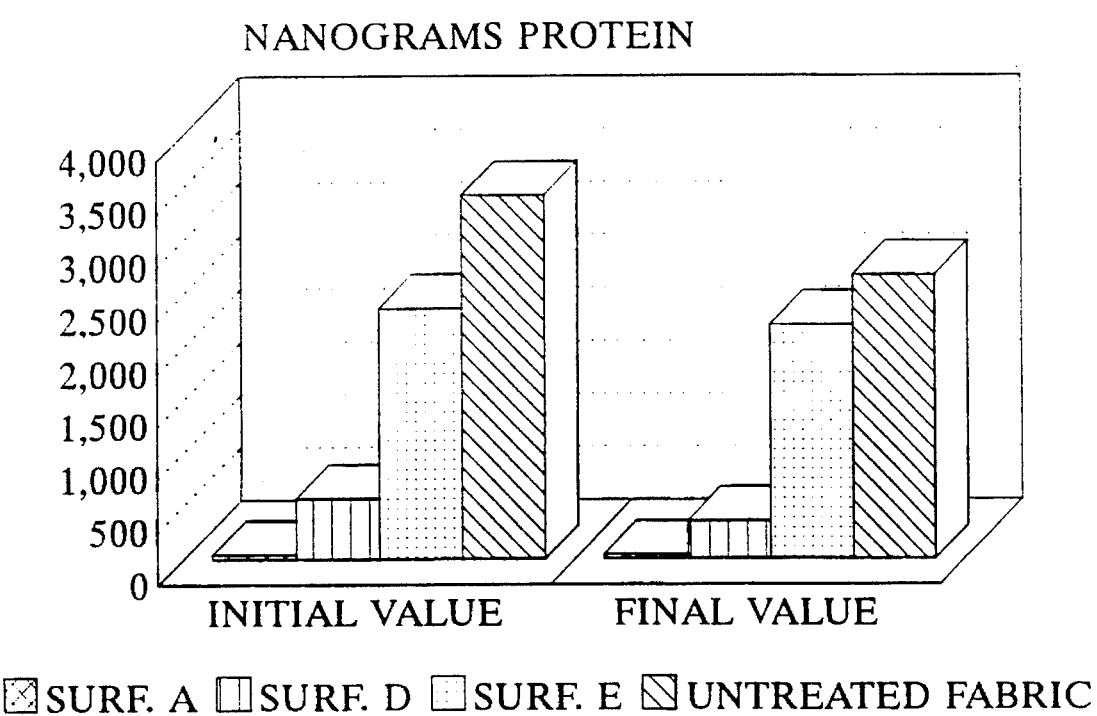
FIG. 11 is a three-dimensional bar graph showing initial and final amounts of protein adsorbed as measured by a radiolabeling technique on washed polymeric fabrics to which three different surfactants had been applied prior to washing.

From the data in the table, it is clear that Surfactant A not only is superior to Surfactants D and E in providing a protein antifouling surface, but also almost completely blocks the adsorption of protein by the fabric. Equally important is the fact that Surfactant A provides an effective protein antifouling fabric even though the coated fabric was subjected to a rigorous washing procedure, thereby demonstrating the durable protein antifouling properties of the coated fabric. To more clearly illustrate such superiority, the data in Table 7 were plotted as a three-dimensional bar graph which is shown in FIG. 11. Although Surfactant D significantly reduced protein adsorption, a much higher level of protein adsorption was observed in repeat experiments.

EXAMPLE 4

Demonstration of Surfactant Durability on Substrates

A low density polyethylene film having a thickness of about 11 mils (about 0.28 mm, Cadillac Plastic, Seattle, Washington) was cut into a number of 11×50 mm strips. Each strip was cleaned by placing it in a test tube, adding methylene chloride to each tube in an amount sufficient to cover the film, covering each tube with aluminum foil, and sonicating each tube for 15 minutes. The solvent was removed from the tubes. The procedure was repeated sequentially with acetone and then with water. The strips were removed from the test tubes and placed in a vacuum desiccator for drying and storage.

A variety of surfactants were studied, including Surfactants A, D, and E from Example 3. Surfactants B and C from Example 2 were not tested as they are known to have little or no substantivity on the substrates employed in this example. The other surfactants included in the study were as follows:

Surfactant F: A polysiloxane polyether similar to Surfactant D, Silwet® L-7001 (Union Carbide Corporation, Danbury, Conn.).

Surfactant G: A polysiloxane polyether similar to Surfactant D, Silwet® L-7604 (Union Carbide Corporation, Danbury, Conn.).

Surfactant H: A polysiloxane polyether similar to Surfactant D, Silwet® L-7605 (Union Carbide Corporation, Danbury, Conn.).

Surfactant I: A polysiloxane polyether similar to Surfactant D, Silwet® L-7614 (Union Carbide Corporation, Danbury, Conn.).

Surfactant J: A polysiloxane polyether similar to Surfactant D; the material had a weight-average molecular weight of about 4,800, about 18 dimethylsilyleneoxy groups, about 5 polyether-substituted methylsilyleneoxy groups, and the polyether side chains consisted of 100 percent by weight ethylene oxide with about 12 ethylene oxide repeating units terminated by hydrogen.

Surfactant K: A polysiloxane polyether similar to Surfactant D; the material had about 13 dimethylsilyleneoxy groups, about 5 polyether-substituted methylsilyleneoxy groups, polyether side chains consisting of 100 percent by weight ethylene oxide terminated by hydrogen, a cloud point of about 90° C. (1 percent solution in water), a refractive index at 20° C. of 1.455, a specific gravity at 25° C. of 1.070 g/cm$^3$, and a viscosity at 25° C. of 360 mm$^2$/sec.

Surfactant L: A polysiloxane polyether similar to Surfactant D; the material had a weight-average molecular weight of about 850, no dimethylsilyleneoxy groups, about 2 polyether-substituted methylsilyleneoxy groups, and the polyether side chains consisted of 100 percent by weight ethylene oxide terminated by a methyl group.

Surfactant M: A polysiloxane polyether similar to Surfactant E, having a number-average molecular weight of about 5,300 and the polyether side chains consisting of 100 percent by weight ethylene oxide with about 12 ethylene oxide repeating units; the material had a cloud point of about 80° C. (4 percent solution in water), a refractive index at 20° C. of 1,450, a specific gravity at 25° C. of 1.060 g/cm$^3$, and a viscosity at 25° C. of 550 mm$^2$/sec.

Surfactant N: A polysiloxane polyether similar to Surfactant E, having a number-average molecular weight of about 6,000 and the polyether side chains consisting of 20 percent by weight ethylene oxide and 80 percent by weight propylene oxide; the material had a cloud point of about 10° C. (1 percent solution in water), a refractive index at 20° C. of 1.444, a specific gravity at 25° C. of 1.011 g/cm$^3$, and a viscosity at 25° C. of 300 mm$^2$/sec.

Surfactant P: A polysiloxane polyether similar to Surfactant E, having a number-average molecular weight of about 6,200 and the polyether side chains consisting of 85 percent by weight ethylene oxide and 15 percent by weight propylene oxide; the material had a cloud point of about 84° C. (1 percent solution in water), a refractive index at 20° C. of 1.449, a specific gravity at 25° C. of 1.075 g/cm$^3$, and a viscosity at 25° C. of 730 centistokes.

In every case, a surfactant solution contained 1 percent by weight of surfactant, based on the weight of the water. Strips were immersed in a surfactant solution for 5–10 minutes, removed, and allowed to air dry. At least one piece of each strip was analyzed for silicon-carbon (Si/C) ratios by electron spectroscopy for chemical analysis (ESCA). The ESCA data were obtained by Evans East, Plainsboro, N.J. The instrument employed was a Perkin-Elmer PHI Model 5000LS ESCA spectrometer utilizing a standard magnesium x-ray source. Source power was 400 watts. The analysis region was 1×3 mm and the exit angle was 45°. All samples were examined initially with low resolution survey scans to determine which elements were present and to establish initial atomic concentrations. High resolution ESCA multiplex data were taken to determine the atomic concentration and binding energy of the elements detected in the survey scans.. A second survey spectrum was then collected to verify that sample damage had not occurred during acquisition of the multiplex data. The quantitation of the elements was accomplished by using the ESCA spectrometer as configured. Approximate sampling depth was 55 Å relative to carbon electrons.

The strips then were subjected to the rigorous washing routine described in Example 3. Briefly, each strip of film was placed in a 10-ml test tube, soaked for no less than 30 minutes in distilled water at ambient temperature, followed by a two-hour soaking in additional fresh distilled water. The film then was rinsed three times with fresh distilled water and allowed to dry. Each film was analyzed again for silicon-carbon ratios by ESCA. In addition, pieces of the 11×50 mm samples of the fabric of Example 3 were subjected to the same procedure and analyzed after being treated separately with Surfactants A, D, and E as described above for the film samples. The results are summarized in Table 8.

TABLE 8

Summary of ESCA Analyses of Film and Fabric Samples

| Substrate | Surfactant | ESCA Si/C Ratio | |
|---|---|---|---|
| | | Before Wash | After Wash |
| Film | A | 0.26 | 0.22 |
| Film | D | 0.18 | 0.03 |
| Film | E | 0.12 | 0.06 |
| Film | F | 0.12 | 0.07 |
| Film | G | 0.12 | 0.01 |
| Film | H | 0.11 | 0 |
| Film | I | 0.11 | 0 |
| Film | J | 0.13 | 0.01 |
| Film | K | 0.12 | 0 |
| Film | L | 0.07 | 0 |
| Film | M | 0.04 | 0.01 |
| Film | N | 0.11 | 0.01 |
| Film | P | 0.09 | 0 |
| Fabric | A | 0.26 | 0.26 |
| Fabric | D | 0.17 | 0.08 |
| Fabric | E | 0.16 | 0.08 |

From the data in Table 8, it is evident that only a surfactant coming within the scope of the present invention is durable on the substrates tested. That is, only Surfactant A substantially remains on the substrate when subjected to a rigorous washing procedure. This conclusion is consistent with the results of Examples 1 and 3 which demonstrated the ability of Surfactant A to provide durable wettability and durable protein antifouling properties, respectively.

Having thus described the invention, numerous changes and modifications thereof will be readily apparent to those having ordinary skill in the art without departing from the spirit or scope of the invention.

What is claimed is:

1. A method of durably rendering a polymeric fabric wettable and resistant to protein adsorption which comprises:

providing a polyolefin fabric having a surface;

applying to the surface of the polyolefin fabric a composition comprising water and a surfactant; and drying the polyolefin fabric to which the composition has been applied; in which the surfactant has a solubility in water at 20° C. no greater than about 5 percent by weight, based on the weight of the water, is present on the fabric in an amount of at least 0.3 percent by weight, based on the weight of the fabric, to durably render the polyolefin fabric wettable and resistant to protein adsorption; and has the formula,

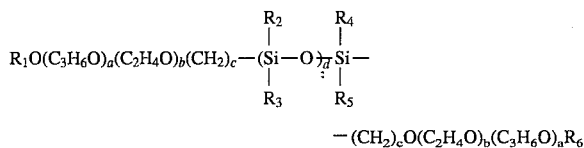

wherein:

each of $R_1$ and $R_6$ independently is selected from the group consisting of hydrogen and $C_1$–$C_8$ alkyl and aryl groups;

each of $R_2$–$R_5$ independently is selected from the group consisting of $C_1$–$C_8$ alkyl and aryl groups;

a represents an integer from about 8 to about 25;

b represents an integer from about 8 to about 25;

the ratio of b to a is in a range of from about 0.7 to about 1.5;

c represents an integer from 1 to about 10;

d represents an integer from about 40 to about 100;

the ratio of d to two times the sum of a and b is in a range of from about 0.7 to about 1.5; and the number-average molecular weight of the surfactant is in a range of from about 5,000 to about 35,000.

2. The method of claim 1, in which:

each of $R_1$ and $R_6$ independently is selected from the group consisting of hydrogen and $C_1$–$C_3$ alkyl and phenyl groups;

each of $R_2$–$R_5$ independently is selected from the group consisting of $C_1$–$C_3$ alkyl and phenyl groups;

a represents an integer from about 12 to about 18;

b represents an integer from about 12 to about 18;

the ratio of b to a is about 1;

c represents an integer from about 2 to about 4;

d represents an integer from about 50 to about 70;

the ratio of d to two times the sum of a and b is about 1; and the number-average molecular weight of said first surfactant is in a range of from about 6,500 to about 18,500.

* * * * *

UNITED STATES PATENT AND TRADEMARK OFFICE
CERTIFICATE OF CORRECTION

PATENT NO. : 5,500,254
DATED : 03/19/96
INVENTOR(S) : R. B. Quincy, III, R. S. Nohr, J. G. MacDonald, E. D. Gadsby It is certified that error appears in the above-identified patent and that said Letters Patent is hereby corrected as shown below:

Column 4, line 64, "reelamine" should read --melamine--;
Column 15, line 30, "et at." should read --et al.--;
Column 15, line 57, "Bergstrom" should read --Bergström--;
Column 16, line 19, "370C" should read --37°C--
Column 16, line 28, "Bergstr6m" should read --Bergström--;
Column 16, line 43, "soakrinse" should read --soak-rinse--.

Signed and Sealed this

Sixth Day of August, 1996

Attest:

BRUCE LEHMAN

Attesting Officer — Commissioner of Patents and Trademarks